(12) United States Patent
Bernasconi et al.

(10) Patent No.: US 12,144,692 B2
(45) Date of Patent: Nov. 19, 2024

(54) ASSISTED TIGHTENING DEVICE FOR HANDPIECE

(71) Applicant: BIEN-AIR HOLDING SA, Biel/Bienne (CH)

(72) Inventors: Fabio Bernasconi, Péry (CH); Davide Sarchi, Zürich (CH); Sébastien Juillerat, Moutier (CH); Gaël Guerlesquin, Fontainemelon (CH)

(73) Assignee: BIEN-AIR HOLDING SA C/O BIEN-AIR DENTAL SA, Biel/Bienne (CH)

( * ) Notice: Subject to any disclaimer, the term of this patent is extended or adjusted under 35 U.S.C. 154(b) by 630 days.

(21) Appl. No.: 17/436,712

(22) PCT Filed: Mar. 30, 2020

(86) PCT No.: PCT/EP2020/058910
§ 371 (c)(1),
(2) Date: Sep. 7, 2021

(87) PCT Pub. No.: WO2020/201193
PCT Pub. Date: Oct. 8, 2020

(65) Prior Publication Data
US 2022/0168067 A1   Jun. 2, 2022

(30) Foreign Application Priority Data
Mar. 29, 2019 (EP) ..................................... 19166219

(51) Int. Cl.
*A61C 1/14* (2006.01)
*A61B 17/16* (2006.01)
*A61C 1/05* (2006.01)

(52) U.S. Cl.
CPC ............ *A61C 1/144* (2013.01); *A61B 17/162* (2013.01); *A61C 1/05* (2013.01); *A61C 2201/00* (2013.01)

(58) Field of Classification Search
CPC ....... A61C 1/144; A61C 1/05; A61C 2201/00; B23B 23/0035; B23B 23/0042;
(Continued)

(56) References Cited

U.S. PATENT DOCUMENTS

| 4,536,157 A | 8/1985 | Maizenberg |
| 10,307,896 B2 * | 6/2019 | Shu ..................... B25B 23/0035 |
| 2009/0176187 A1 | 7/2009 | Esposti et al. |

FOREIGN PATENT DOCUMENTS

| EP | 0374276 A1 | 6/1990 |
| EP | 0273259 A1 | 3/1991 |

(Continued)

OTHER PUBLICATIONS

International Search Report & Written Opinion in PCT/EP2020/058910 dated Jul. 20, 2020, 11 pages.

*Primary Examiner* — Jacqueline T Johanas
*Assistant Examiner* — Drew S Folgmann
(74) *Attorney, Agent, or Firm* — Tucker Ellis LLP (57) ABSTRACT

The present invention relates to a chucking device for a drilling tool for a dental handpiece, as well as a handpiece for dental or surgical applications comprising:—a head (10) in which is inserted in removable fashion a drilling tool (100) able to be actuated in rotation about an axis of rotation (R) by means of a drive mechanism comprising a drive shaft (2) rotating about this axis of rotation (R)—a clamping device for the drilling tool (100), comprising a chucking clamp (4) disposed inside said drive shaft (2) for axial retention of the drilling tool (100) with respect to the axis of rotation (R), the clamp (4) co-operating with a plunger (5), and—a push-button (61) arranged to act upon the plunger
(Continued)

(5) in order to release the drilling tool (100); The handpiece (1) contains a permanent magnet (7) arranged symmetrically around the axis of rotation (R) and exerting a force of magnetic attraction (F) on the plunger (5) in direction of the push-button (61).

15 Claims, 10 Drawing Sheets

(58) Field of Classification Search
CPC .............. B23B 23/0007; B23B 23/003; Y10T 279/3481; A61B 17/1622; A61B 17/162
See application file for complete search history.

(56) References Cited

FOREIGN PATENT DOCUMENTS

| | | |
|---|---|---|
| FR | 2573303 A1 | 5/1986 |
| JP | 2002095679 A | 4/2002 |

* cited by examiner

FIG. 13

ASSISTED TIGHTENING DEVICE FOR HANDPIECE

TECHNICAL FIELD

This invention relates to the field of turbines and contra-angles, more specifically to chucking devices for a drilling tool.

STATE OF THE ART

The majority of high-speed dental handpieces on the market, i.e. (air-fed) turbines and multiplier contra-angles (fed by electric motors) are equipped with a system for clamping the drill based on the use of a resilient clamp. This system has been well known for a very long time, in particular the solution as described in the patent document EP0273259B1.

In clamping systems of this type, the rotor shaft (on which and on the outside of which one press-fits either the turbine, in the case of an air turbine, or the transmission pinion, in the case of a contra-angle) driving in rotation the drilling tool contains a clamp and a plunger. The clamp is generally press-fitted and/or welded into the shaft, and it has two functions: that of axially retaining the drill, by means of the flexible elastic ends, and that of guiding the drill radially so as to prevent, in the presence of applied radial load by the dentist during the drilling, the drill from being excessively inclined and able to generate excessive vibrations detrimental to the precision of the work. The plunger is itself partially free in the shaft because it can slide axially in the shaft and in certain cases can turn angularly in the shaft (in the case of a conical plunger); it co-operates with the clamp in the opening phase of the clamp to release the drill when the surgeon-dentist pushes on the release button which covers the plunger. When the clamp is closed and grips the drill, the plunger can be in simple abutment on a surface of the clamp but must never exert an opening force on the resilient parts of the clamp.

In order to prevent, during the drilling and owing to an excessive axial load applied by the surgeon-dentist on the drill, the drill from being able to slide beyond the clamp's jaws toward the cover and block the plunger, making it thus impossible for the user to push the plunger against the applied pressure on the cover and to open the clamp to remove the drill at the end of the work, there exist furthermore perfected clamping systems comprising an additional component which will be referred to as a clamping stop. Such a component is introduced, preferably press-fitted and/or welded or soldered in the shaft on the side of the cover of the head of the handpiece, and it makes it possible to prevent any axial blockage of the plunger. The presence of the clamping stop thus limits the returns to the manufacturer due to a drill that is jammed in the clamp.

However, none of these solutions of the state of the art makes it possible to effectively prevent the plunger from accidentally forcing the clamp to open during rotation and drilling, in particular because of vibrations or shocks when the material to be drilled is particularly hard.

The use of permanent magnets in heads of dental handpieces is otherwise known as well. Patent document EP0374276 discloses for example permanent magnets used within seal means preventing cooling water from reaching upper and lower bearings, whereby a magnetic fluid arranged between the permanent magnets are intended to ensure a frictionless contact between a support driven in rotation and a fixed cap.

The patent document FR2573303 relates to a lever actuated clamp for holding a drilling tool, whereby a magnet is foreseen to secure the lever in an inactive position onto an outer cap.

None of these two solutions can solve the above mentioned problem of clamping reliability of the drilling tool during operation either.

Thus there exists a need for solutions free of these known limitations.

SUMMARY OF INVENTION

One object of the present invention is thus to propose a new clamping device which is more effective and more reliable.

Another object of the present invention is to propose a perfected clamping device that nevertheless remains compatible with the heads of standard handpieces, and which does not make the assembly of the button-plunger used for release more complex.

These objects are achieved by means of the features of the main claim, and in particular by means of the fact that the handpiece contains a permanent magnet designed symmetrically around the axis of rotation and which exerts a force of magnetic attraction on the plunger in the direction of the push-button.

Advantageously, the permanent magnet is designed and arranged so as never to be in contact with the plunger, whereby an air gap is provided between the permanent magnet and the plunger.

An advantage of the proposed solution is that it allows the plunger to be kept, through magnetic force, in a raised position with respect to the clamp, which makes it possible to improve the robustness of the clamping, even in the case of major shocks sustained by the drill during drilling, which can therefore only with greater difficulty cause the jamming of the plunger in the clamp, and even less so bring about the opening of the chuck leading to the ejection of the drill.

At the same time, the proposed solution makes it possible to improve the reliability of the clamping while also minimizing the additional components to be introduced into the construction of the handpiece, without impacting the operations of assembly of the latter.

According to a preferred embodiment, the arrangement of the permanent magnet in the retaining nut of the push-button furthermore makes it possible to provide additional safety against any untimely opening of the chuck, because of an unintentional pressure exerted on the push-button, owing to the magnetic force which must be overcome in addition to the resilient return force exerted by the spring.

According to several variants, the geometry of the plunger can moreover be adapted to maximize the force of attraction vis-a-vis the magnet, in particular with the aid of peripheral annular protrusions oriented in the vertical or radial direction, in order to bring them closer together, according to the needs, or with the aid of a cap, provided with a peripheral annular bead, covering the plunger.

According to another advantageous variant, the magnet is covered with a ferromagnetic material for shielding purposes, thus making it possible to minimize the effects of the magnetic field generated by the magnet in relation to the outside, as well as to minimize interference due to external fields.

In yet another advantageous variant, all the components located in the vicinity of, or just near the permanent magnet or the plunger are preferably not ferromagnetic.

BRIEF DESCRIPTION OF THE DRAWINGS

The present invention will be better understood with a reading of the description which will follow, given by way of example and with reference to the drawings in which.

DETAILED DESCRIPTION OF THE INVENTION

Within the context of this application, the handpiece in which the clamping mechanism according to the invention is integrated can consist either of a "turbine", when the drill is driven in rotation under the action of compressed air injected by means of a pipe, or can consist of a "contra-angle" using a drive shaft actuated by a motor.

Figure 1:
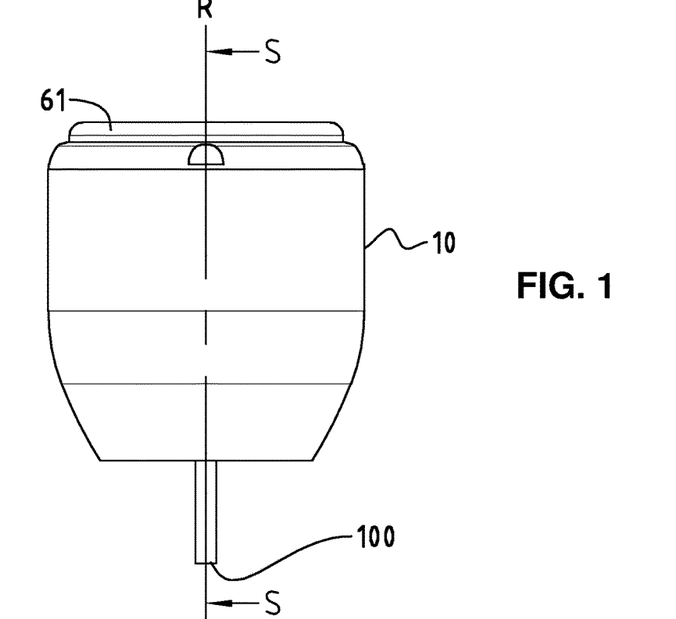
FIG. 1 is a front view of the head of a handpiece provided with a drilling tool according to a preferred embodiment for the present invention.

Illustrated precisely in FIG. 1 is a view of the outside of a handpiece 1, able to consist of a turbine or a contra-angle. It comprises a head 10 at the base of which the drill 100 is inserted, mounted in a way rotating about its axis of rotation R. A push-button 61 covering the head 10 makes it possible in a conventional way to release the drill 100 when pressure is exerted on it by the user of the handpiece, that is to say typically the surgeon-dentist.

The arrows S-S of FIG. 1 indicate the sagittal cutting plane to be used in following FIGS. 2 to 10 to make it possible to display in more detail the mechanism for mounting and clamping of the drill 100 proposed in the context of the present invention, first of all in the context of a turbine (in FIGS. 2 to 7) then in the context of a contra-angle.

In the following, first of all, a first preferred embodiment connected with a turbine will be described, with reference to FIGS. 2 to 4.

Figure 2:
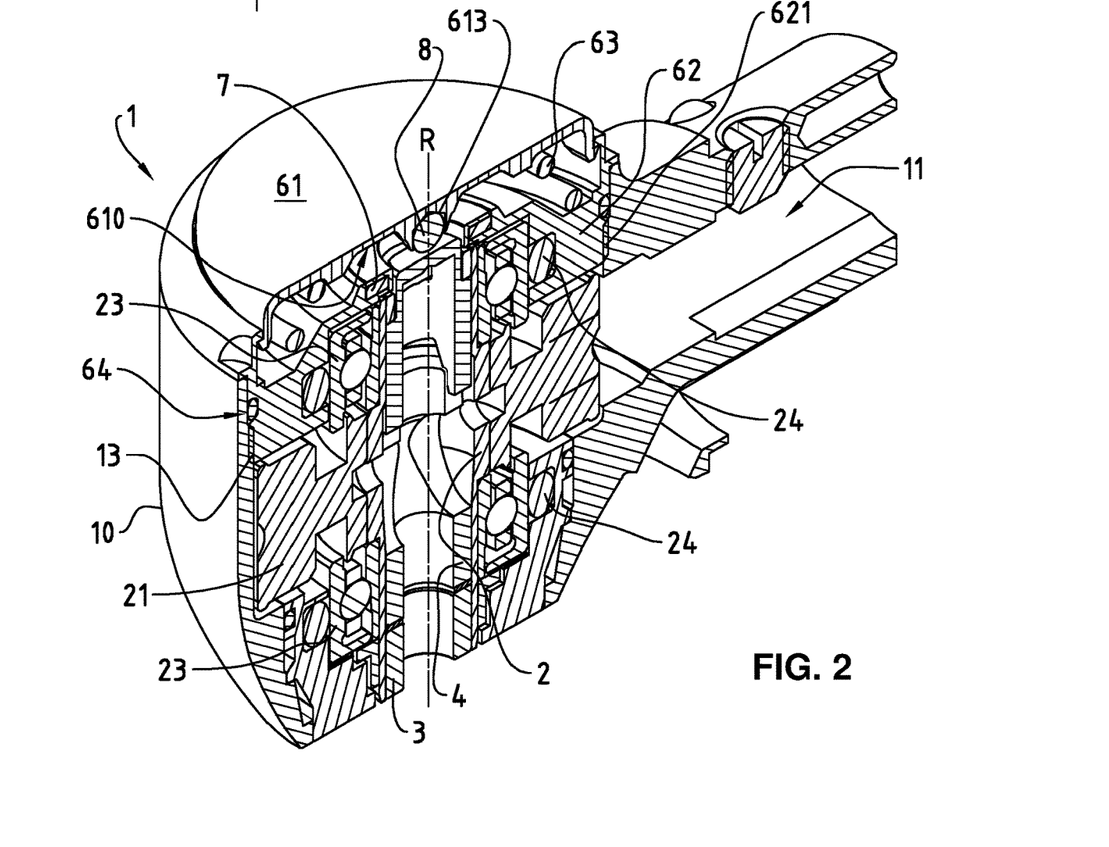
FIG. 2 is a partial sagittal sectional view, along the cutting plane (S-S) indicated in FIG. 1, in three dimensions, of a handpiece using a turbine provided with a clamping system according to a preferred embodiment of the present invention.

FIG. 2, which consists of a partial sagittal sectional view in three dimensions of a handpiece 1 along the cutting plane (S-S) indicated in FIG. 1, makes it possible to distinguish the different usual elements of a head 10 and of a clamping mechanism for the drill 100 not shown however for the sake of clarity comprising notably the pipe for supply of compressed air 11 on the right in the Figure, driving the turbine 21, itself integral in rotation with a drive shaft 2 for the drilling tool 100, which is commonly referred to as being "the rotor shaft". The drive shaft 2 here is inserted between two bearings 23, preferably ball bearings, themselves squeezed by respective gaskets of O-ring type 24. Mounted in the drive shaft 2 are respectively the axial retaining clamp 4 for the drill—the jaws of which are not visible in this figure, but better seen in FIG. 10 relating to a corresponding embodiment for a contra-angle—and the radial guide bush 3, these two pieces being separated in order to be able in particular to adjust the materials used for the clamp 4 to those of the guide bush 3. Therefore, whereas the clamp 4 requires preferably resilient and deformable materials, the bush 3 requires, for its part, preferably very hard materials, so as to be wear-resistant and to ensure excellent features for guiding along the axis of rotation R for as long a time as possible.

Inserted in the upper part of the head is a piece for holding the push-button 61, which is provided to release the drill 100. This holding piece consists, according to the preferred embodiment described, of a nut 62 screwed in the head by means of a threaded bead 621 at its outer periphery, co-operating with an internal threading 13 made in the head 10; a sealing gasket 64 is provided, where these two screwing surfaces co-operate, to ensure the repeatable positioning of the nut and of the push-button and, in the case of a turbine, to thus stabilize the aerodynamic flows exiting from the head. Disposed on top of the retaining nut 62 is a spring 63 making it possible to bring the push-button 61 back into its resting position, as represented in FIGS. 2 and 3, where a peripheral radial engagement part 612 of the push-button is kept in contact against an inner peripheral retaining lip 622, the co-operation of the engagement parts being in evidence in FIG. 3.

In FIG. 2, one can likewise distinguish, at the lower face 610 of the push-button 61, an anti-heating ball 8, made of a material of low thermal conductivity provided for this purpose, and which is preferably press-fitted directly into a central accommodation 613 provided in the push-button 61, here of hexagonal cross section in order to minimize the heat transfer thermal bridges towards the push-button 61.

The push-button module 6, formed by the nut 62 and the push-button 61, as well as the compression spring 63 interposed between the two, is illustrated later in FIG. 3. In FIG. 2, the plunger 5 can nonetheless be distinguished, with which the push-button 61, or here more precisely the ball 8, can be brought into contact when a pressure is exerted in the direction P, visible in FIGS. 3 and 4, and a permanent magnet 7 arranged in the nut 62. In the context of the present invention, the plunger 5 is made of a passive ferromagnetic material, in such a way as to co-operate with the permanent magnet 7.

In the following, reference will be made equally to FIG. 3, taking the same elements as FIG. 2, previously described, in the sagittal plane S-S, and FIG. 4, which shows the detail of the magnifying glass A indicated by a circle in FIG. 3, and which represents the different elements of the perfected clamping device according to the invention in an enlarged view. The description of the references common to all these figures will not be systematically repeated.

Figure 3:
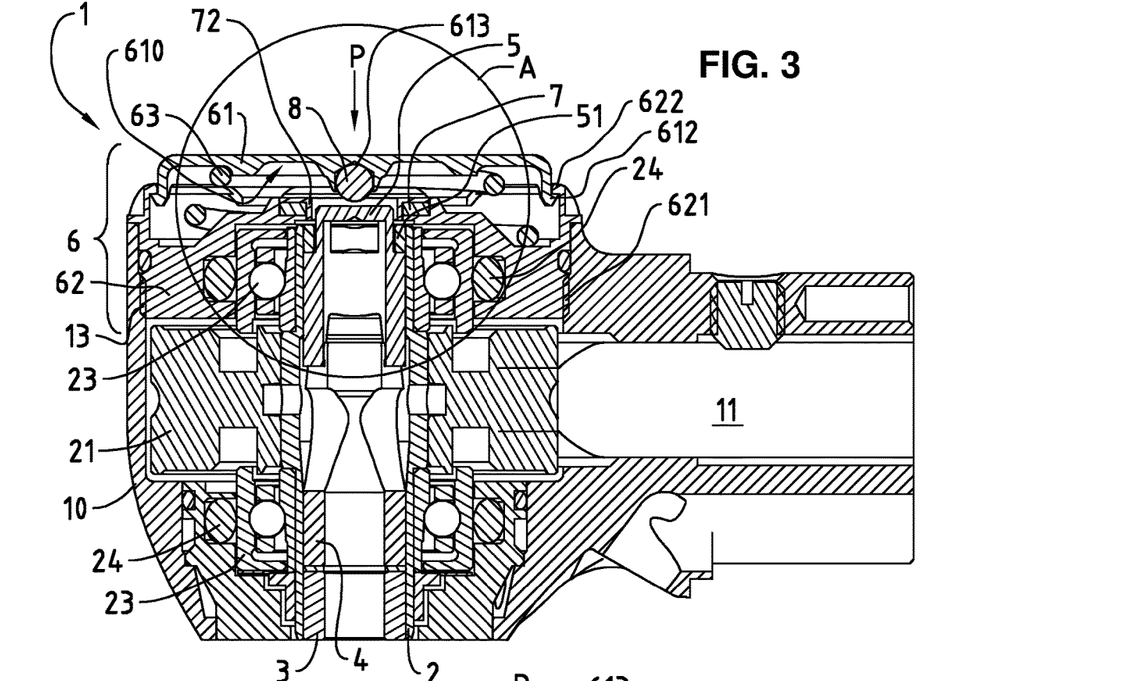
FIG. 3 shows a sectional view of the handpiece of FIG. 2 in the sagittal plane (S-S)
Figure 4:
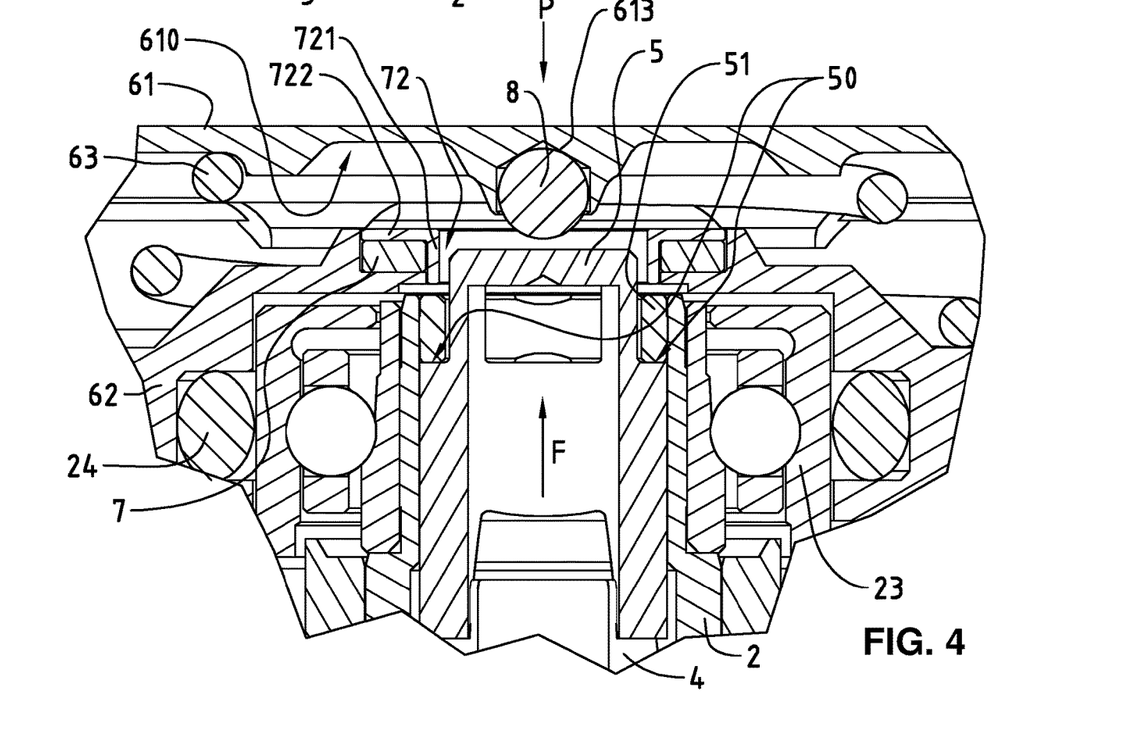
FIG. 4 shows an enlargement of the clamping device indicated by the magnifying glass (A) in FIG. 3.

In FIGS. 2 to 4, it can be noted that a permanent magnet of annular shape 7 is positioned in the retaining nut 62 of the push-button 61 with the aid of a retaining piece 72 having a cylindrical part 721 and an axial retaining collar 722. This piece can be fixed in any manner to the nut 62, for example by press-fitting, welding or soldering, or even screwing, and it can be noted that the positioning of the magnet 7 of annular shape radially extends beyond the casing of the plunger 5, which has moreover peripheral shoulders 50 in order to be able to position the clamping stop 51, of annular shape, above radial recesses. This magnet 7 is magnetized in the axial direction, and thus exerts permanently a force of attraction directed substantially upward on the partner ferromagnetic element, that is to say the plunger 5 of the clamping device. The force of magnetic attraction F is indicated by the arrow in FIG. 4 illustrating the fact that the plunger 5 is kept in upper position in the direction of the push-button 61. In conditions of use, that is to say during the rotation of the drive shaft 2 and the drilling, this magnetic force of attraction F makes it possible to flatten the plunger 5 against the clamping stop 51, and thus prevents the plunger 5 from jamming in the clamp 4 and the latter from opening accidentally. F.

The permanent magnet 7 is, in the context of the present invention, preferably of annular or cylindrical shape, that is to say having a form of revolution about the axis of rotation R of the drill. According to the embodiment illustrated by FIGS. 2 to 4, the fact that the permanent magnet 7 is positioned in the nut 62 has as a consequence to bring the latter as close as possible to its partner ferromagnetic element, i.e. the plunger 5, and thus to maximize the strength of the magnetic force F making it possible to keep it in its "high" position, that is to say the plunger is kept in contact against the clamping stop 51.

This preferred embodiment according to which the permanent magnet 7 is fixed and situated in the retaining nut 62 of the push-button 61 has moreover an additional technical advantage of reliability. In fact, when opening the clamp, the push-button 61 is pressed by the user in direction P, to plunge the plunger 5 inside the clamp 4 and thus open the resilient sleeves of the clamp 4: in this case, the user must overcome not just the holding force of the compressed spring 63 between the nut 62 and the push-button 61, but also the magnetic force F between the plunger 5 and the permanent magnet 7, which adds supplementary security with respect to accidental pressing of the push-button 61 on the part of the user.

Figure 5:
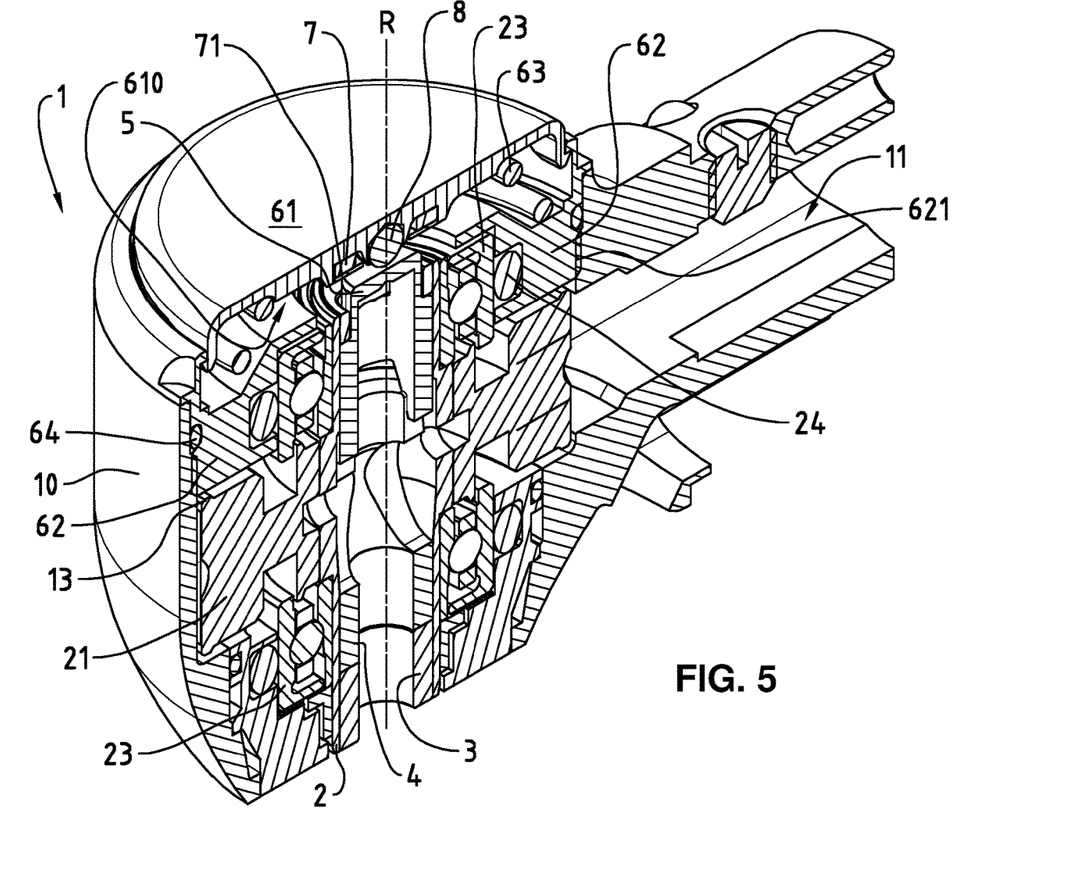
FIG. 5 is a partial sagittal sectional view, in three dimensions, of a handpiece using a turbine provided with a clamping system according to another preferred embodiment of the present invention.
Figure 6:
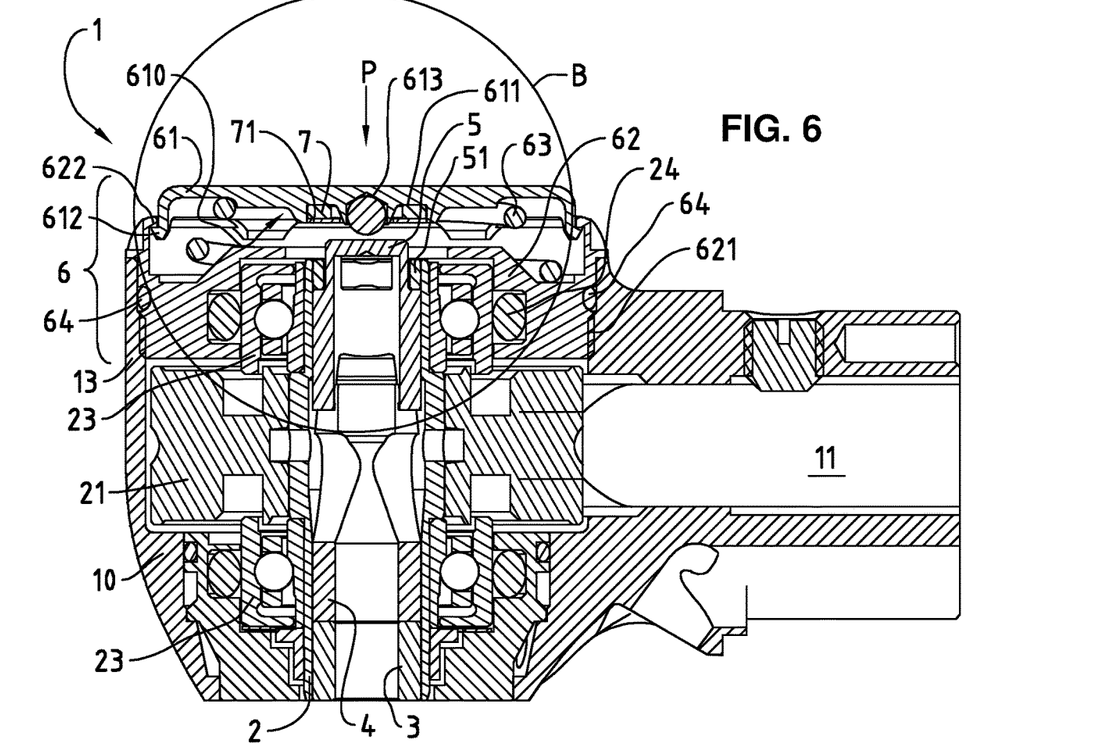
FIG. 6 shows a sectional view of the handpiece of FIG. 5 in the sagittal plane (S-S)
Figure 7:
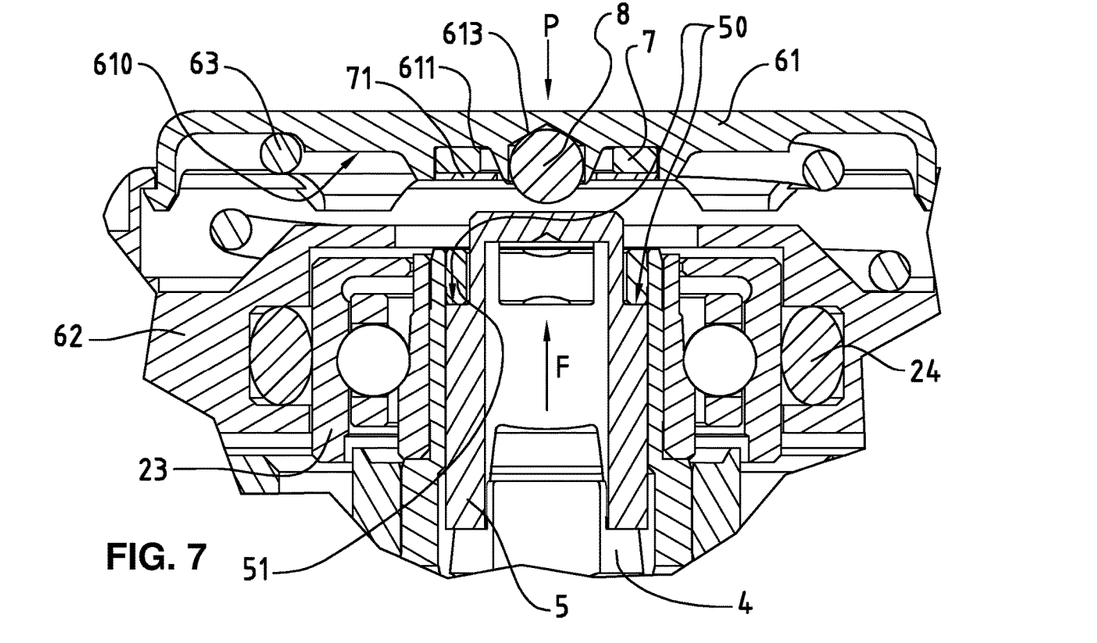
FIG. 7 shows an enlargement of the clamping device indicated by the magnifying glass (B) in FIG. 6.

FIGS. 5 to 7 illustrate another preferred embodiment of the invention, relating to a turbine.

According to this embodiment, the device for driving the drill 100 is in all points identical to that of the previously described embodiment and illustrated by FIGS. 2 to 4; consequently, all the reference numerals introduced in the context of these figures will not be explained again.

However, the device for clamping the drill 100 has a different arrangement of the permanent magnet 7, which this time is no longer integrated in the nut 62, but directly in the push-button. In other words, as can be noted in FIG. 6, a permanent magnet 7 of annular shape is arranged this time around the accommodation 613 of the anti-heating ball 8, in a recess 611 in the lower face 610 of the push-button 61. It is held in position inside the recess of the push-button 61 by an axial retaining washer 71, preferably welded or soldered or glued to the push-button 61. The partner ferromagnetic element of the magnet is once again the plunger 5, represented in FIGS. 5 to 7 in the "high" position, that is to say held in contact against the clamping stop 51 by means of the force of magnetic attraction F indicated by the arrow visible in FIG. 7, and this tends to pull the plunger 5 upward.

The functioning mechanism is similar to that of the preceding embodiment in rotation/drilling mode, where the plunger is brought upward following the magnetic force of attraction F exerted by the magnet. However, a major difference can be noted when there is pressure on the push-button 61, indicated by the arrows P in FIGS. 6 and 7. In other words, during such a phase of pressure on the push-button 61, the magnetic attraction will this time favor a downward movement of the push-button 61 because of the distance between the permanent magnet 7 and the plunger 5, which decreases when the push-button approaches the plunger 5. Consequently, therefore, the intensity of the pressure P which must be applied by the user is less than that in absence of the magnet, whereas it was increased in the preceding case.

However, since in the embodiment of FIGS. 5 to 7, the permanent magnet 7 is located in a position more remote from the plunger 5 than in the embodiment of FIGS. 2 to 4, the force of magnetic attraction F exerted on the plunger 5 will be less, in a way equal to dimensions of the permanent magnet 7 and of the plunger 5. This last embodiment of FIGS. 5 to 7 is, in contrast, easier to achieve because a simple washer can be used to line the permanent magnet. Moreover, in order to increase the magnetic force exerted on the plunger 5, it would be possible furthermore to make the axial retaining washer 71 likewise in a ferromagnetic material, along with the anti-heating ball 8, for example in tungsten carbide with a content of 30% cobalt.

Figure 8:
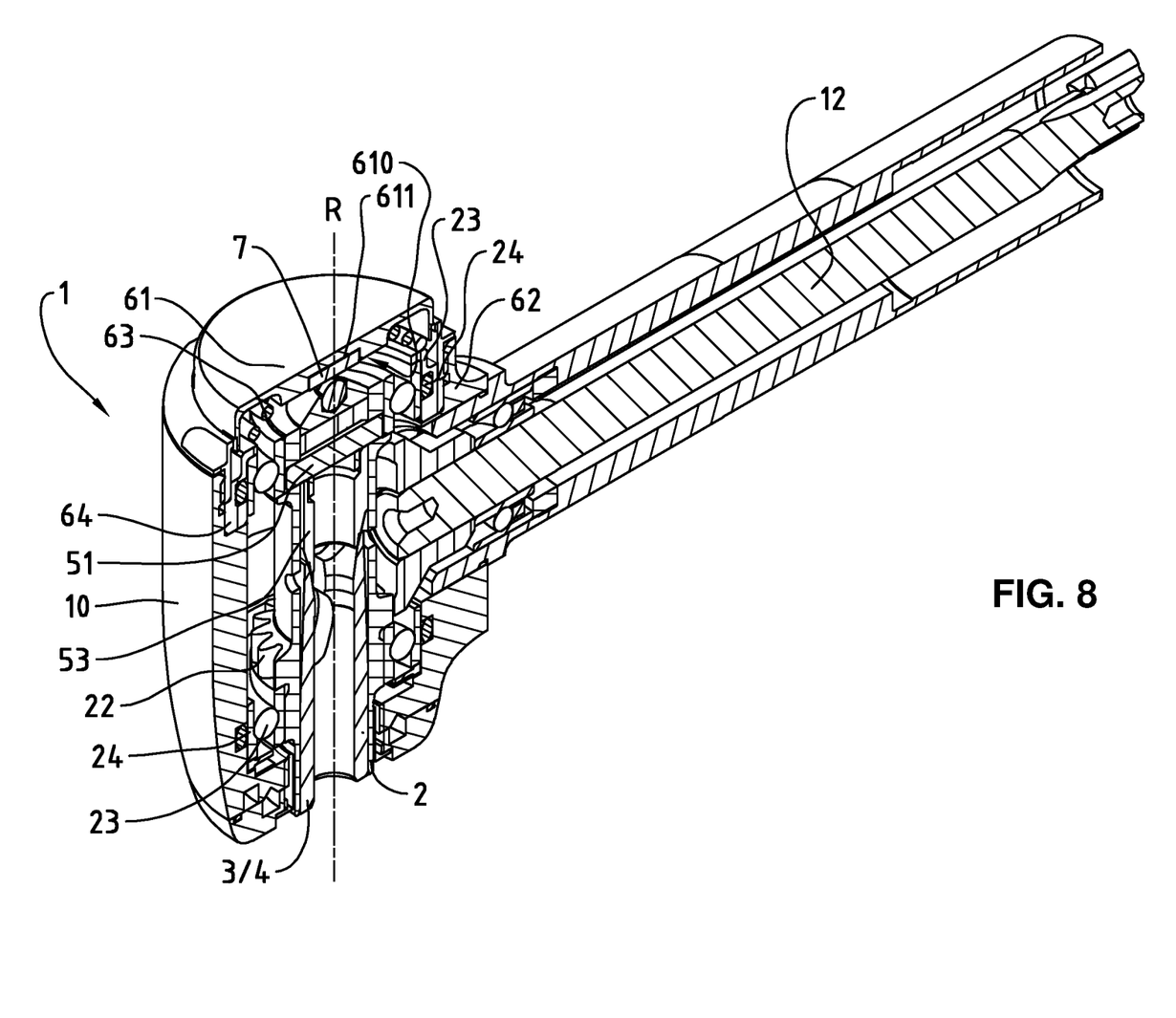
FIG. 8 is a partial sagittal sectional view, in three dimensions, of a handpiece of contra-angle type using not just compressed air, but a drive motor shaft, and which is provided with a system of clamping according to still another preferred embodiment of the present invention.
Figure 9:
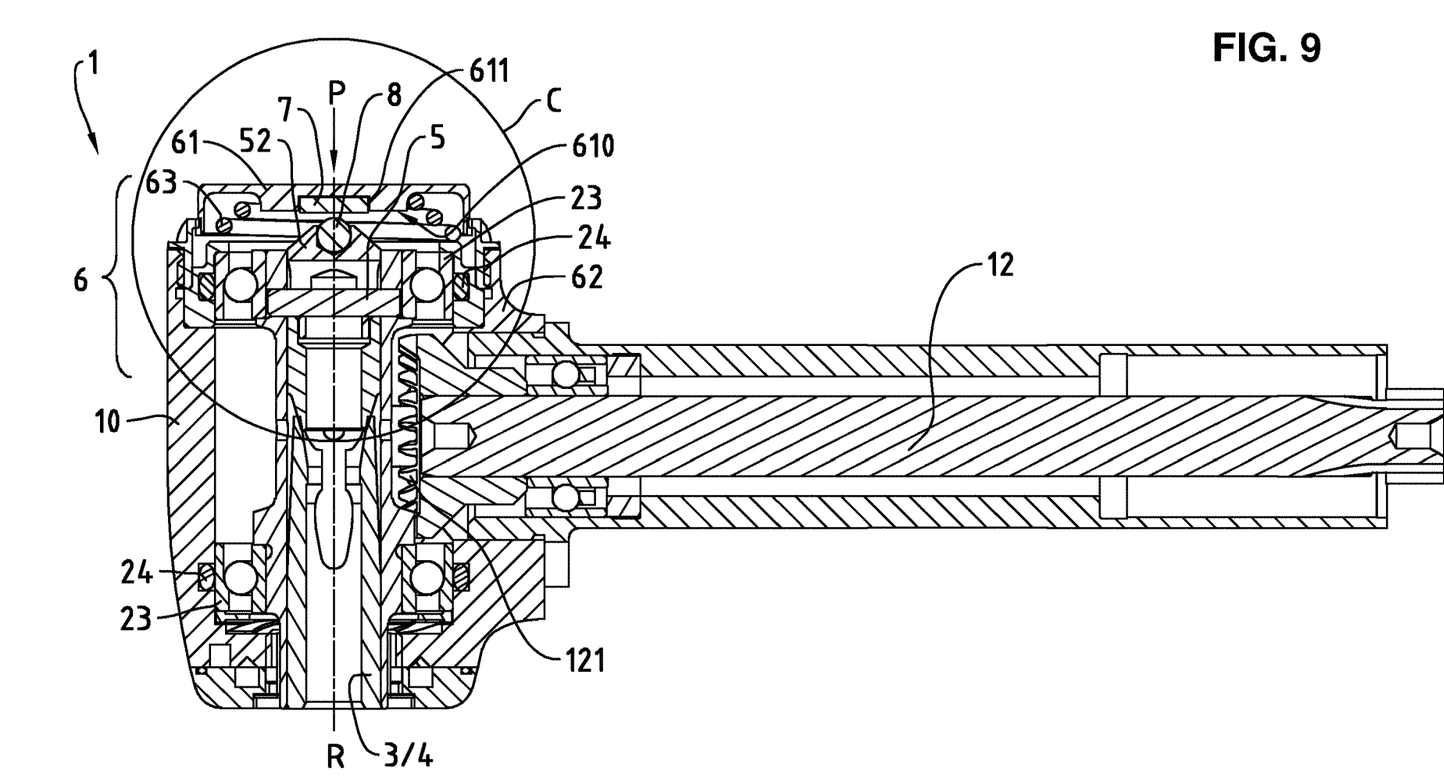
FIG. 9 shows a sectional view of the handpiece of FIG. 8 in the sagittal plane.
Figure 10:
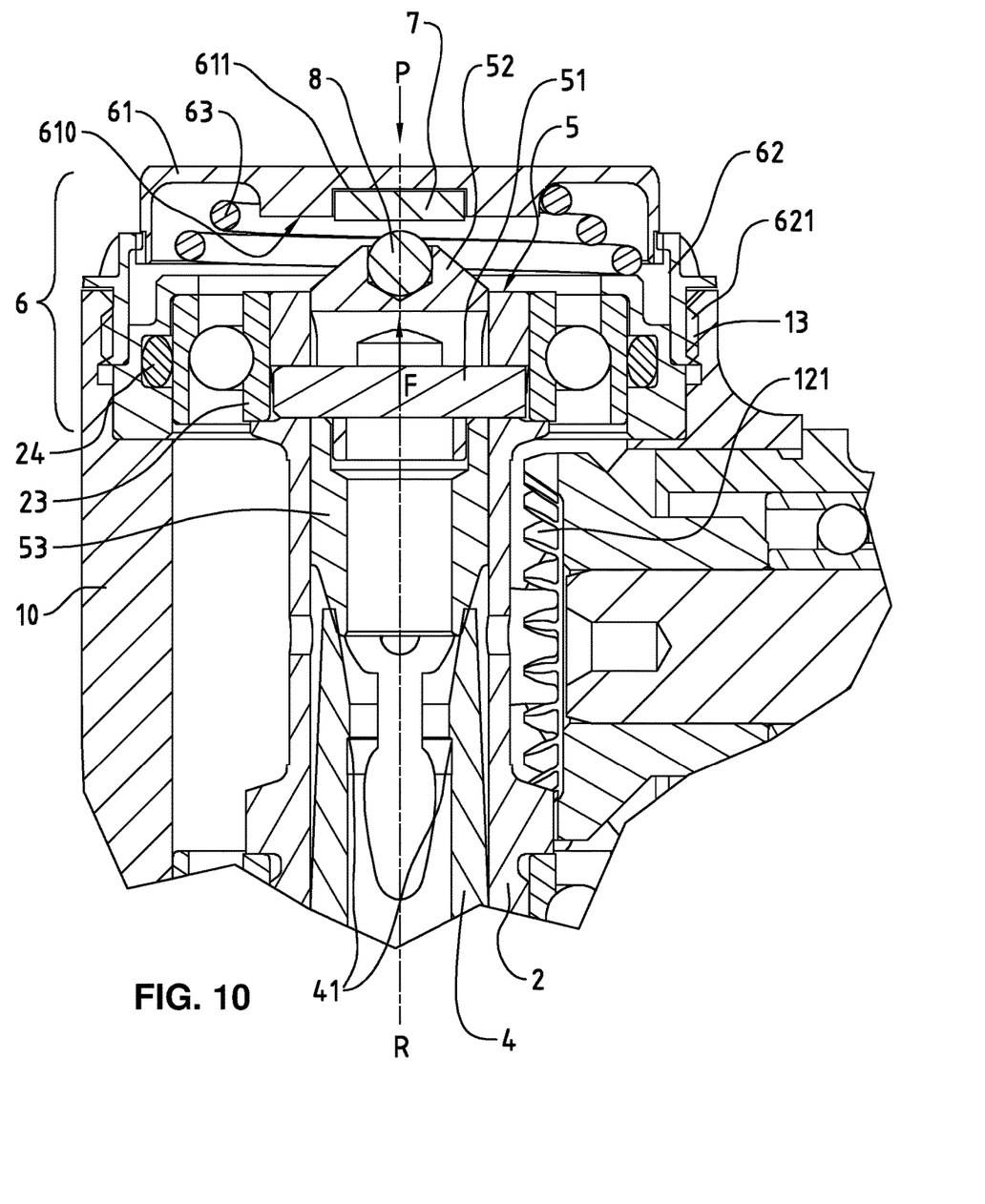
FIG. 10 shows an enlargement of the clamping device indicated by the magnifying glass (C) in FIG. 9.

In addition, according to a variant illustrated by FIGS. 8 to 10 which follow, relating to a contra-angle, the permanent magnet 7 could also take the form of a disk or a pad positioned inside the push-button, but behind the anti-heating ball 8. In such a case, the thickness of the permanent magnet 7 could also be increased in a considerable way so that an increased force of magnetic attraction F results.

FIGS. 8 and 9 show a different embodiment of the rotor shaft, that is to say the drive shaft 2, with respect to the turbine in preceding FIGS. 1 to 7, this time with the aid of a gearing between the motor shaft 12, driven by an electric motor, and the drive pinion 22. The clamping device no longer separates the clamp 4 from the bush 3, but on the contrary, the plunger 5 is from now on achieved in two parts, with an upper part 52 of the plunger 5 which is integral in rotation with the drive shaft 2, because of the clamping stop 51 formed by a transverse pin, and a lower conical part 53 free in rotation with respect to the drive shaft. The permanent magnet 7 formed by the pad disposed in the recess 611 of the lower face 610 of the push-button 61 is from now on able to come into contact with the anti-heating ball 8, provided this time no longer directly in an accommodation of the push-button 61, but on the upper part 52 of the plunger 5.

As can be seen in FIG. 10, which is an enlargement of the encircled part the magnifying glass (C) of FIG. 9, the jaws 45 of the clamp 4 hold axially the drill 100 (not shown so that other parts can be seen more easily) while the lower conical part 53 does not spread them when a pressure is exerted on the push-button 61 toward the inside of the head 10, conforming to the direction of the arrow with the reference symbol "P". In such a case, the passive magnetic element associated with the permanent magnet 7 accommodated in the recess 611 arranged on the lower face of the push-button 61 consists precisely in at least the lower conical part 53, and, because of the axial remoteness of this piece with respect to the permanent magnet 7, potentially also the upper part 52 of the plunger 5.

In the drawings described in the following, a plurality of variants will be given for increasing the force of magnetic attraction F between the permanent magnet 7 and the plunger 5, which constitutes the passive magnetic element according to the invention. It can be noted moreover that to achieve this object, it would be likewise possible, according to a variant, to implement the clamping stop also in a ferromagnetic material.

Figure 11:
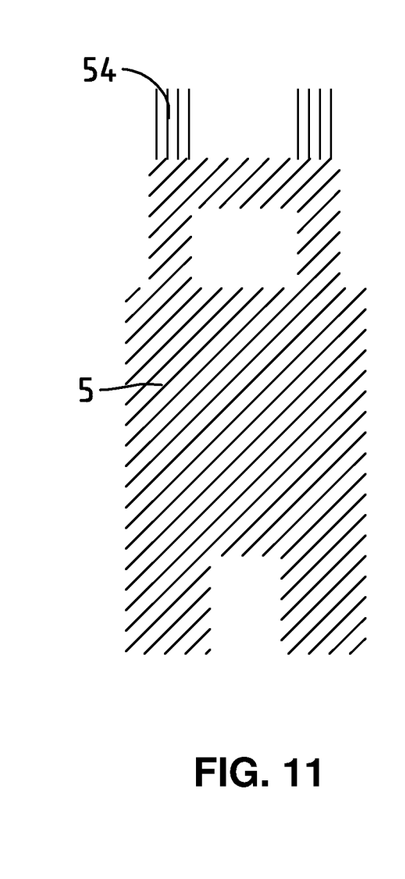
FIG. 11 shows a drawing according to a sectional view of a variant for implementation of the plunger according to the invention, with protruding portions in ferromagnetic material oriented upward.
Figure 11A:
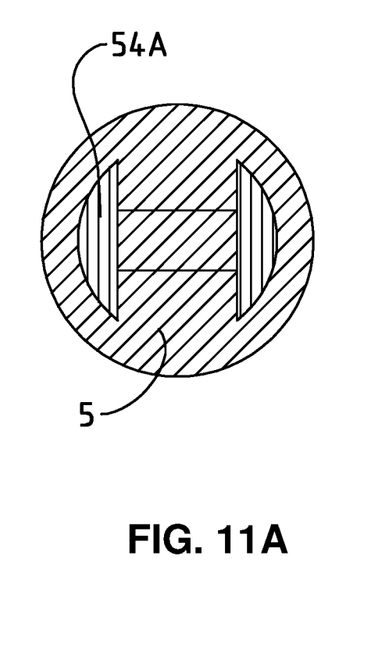
FIGS. 11A and 11B show respectively two top views for alternative implementations of such a plunger.
Figure 11B:
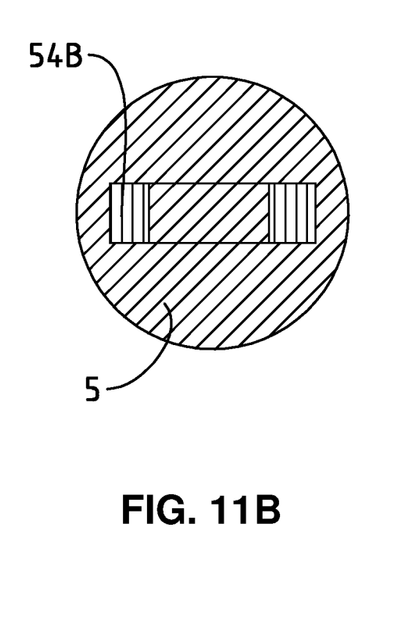

The drawing of FIG. 11 shows a sectional view of a variant for achieving a plunger 5 according to the invention, with first annular protruding portions 54 of ferromagnetic material oriented upward. Such an arrangement of protruding parts forming kinds of horns makes it possible to partially bring closer together the permanent magnet 7 to the plunger 5 and thus to increase the strength of the force of magnetic attraction F. FIGS. 11A and 11B represent respectively two top views for alternative implementation of such a plunger 5 with horns, with two peripheral parts in the shape of a truncated disk 54A arranged symmetrically about the axis of rotation R of the drill, and two rods 54B.

Figure 12:
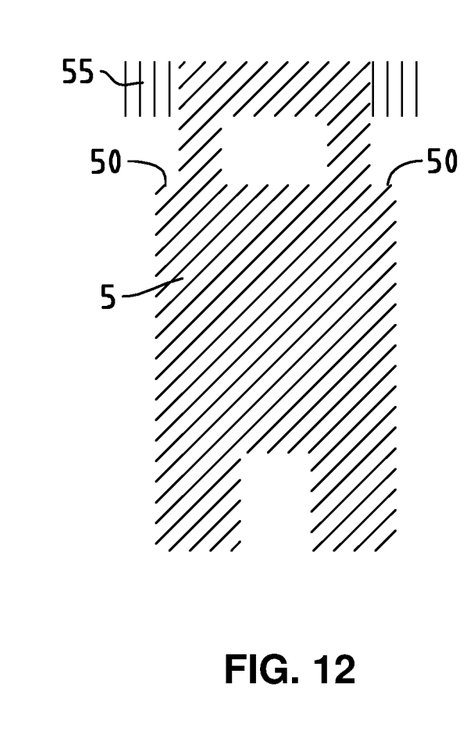
FIG. 12 shows a drawing according to a sectional view of another variant for implementation of the plunger with protruding portions in ferromagnetic material oriented radially.
Figure 12A:
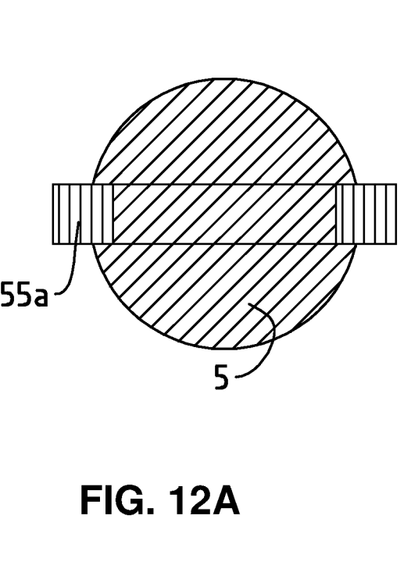
FIGS. 12A and 12B show respectively two top views for alternative implementations of such a plunger.
Figure 12B:
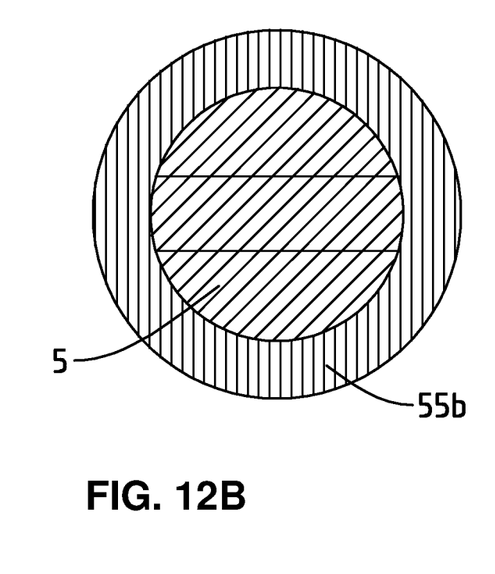

The drawing of FIG. 12 shows a sectional view of another variant for achieving the plunger with second protruding portions 55 of ferromagnetic material, radially oriented this time, which makes it possible to obtain the same advantageous effect of increasing the strength of the force of magnetic attraction F by bringing closer together at least partially the permanent magnet 7 to the plunger 5 by putting it face to face with the permanent magnet according to the embodiment illustrated in FIGS. 2 to 4, as well as 5 to 7. These two protruding portions 55 extend radially beyond shoulders 50 of the plunger 5. FIGS. 12A and 12B represent respectively two top views for alternative implementations of two protruding portions 55A and 55B, corresponding respectively once again to a type of rod, or a collar 55B, for such a plunger 5.

Figure 13:
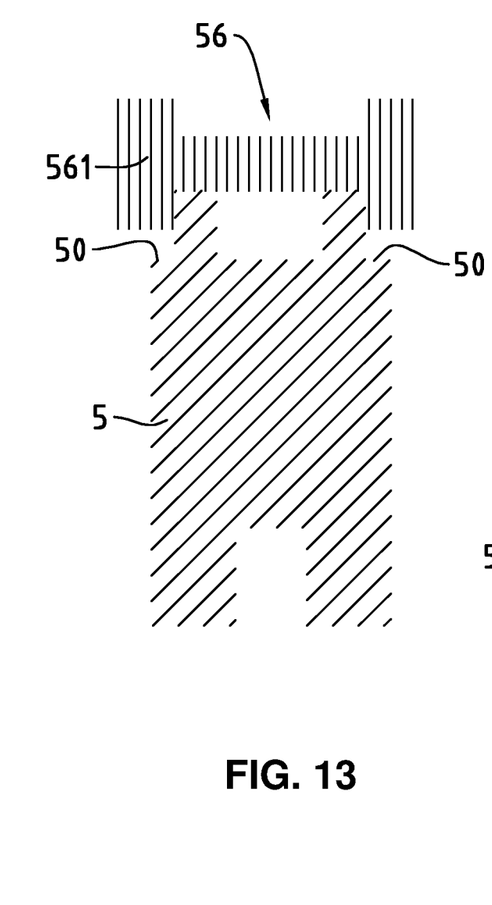
FIG. 13 shows a drawing according to a sectional view of still another variant for implementation of a plunger according to the invention, covered by a cap.
Figure 13A:
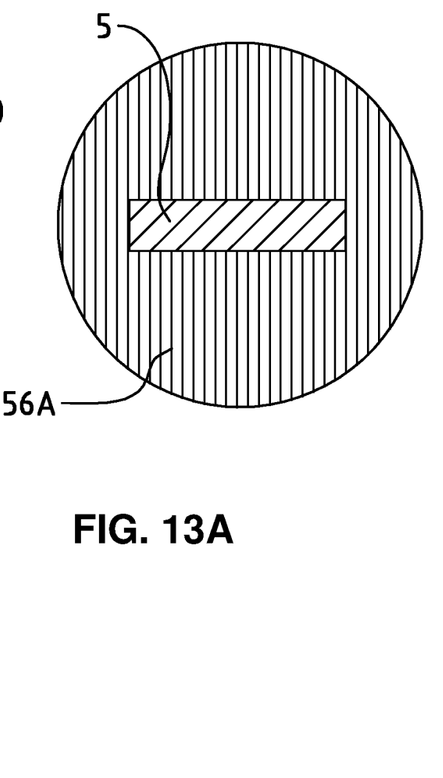
FIG. 13A illustrates a top view corresponding to a possible implementation for such a cap.

FIG. 13 shows a drawing according to a sectional view of still another variant for implementation of a plunger 5 according to the invention, the shape of which makes it possible to bring it closer to the permanent magnet. The plunger 5 this time is covered with a cap 56, of magnetic material, which is provided with an annular bead 561 which extends at the same time in axial direction and in radial direction. Such a variant combines, so to speak, the advantages of the two variants previously described in relation to FIGS. 11 and 12. FIG. 13A illustrates a top view corresponding to a possible implementation for such a cap in the form of an overmolded disk 56A.

Figure 14:
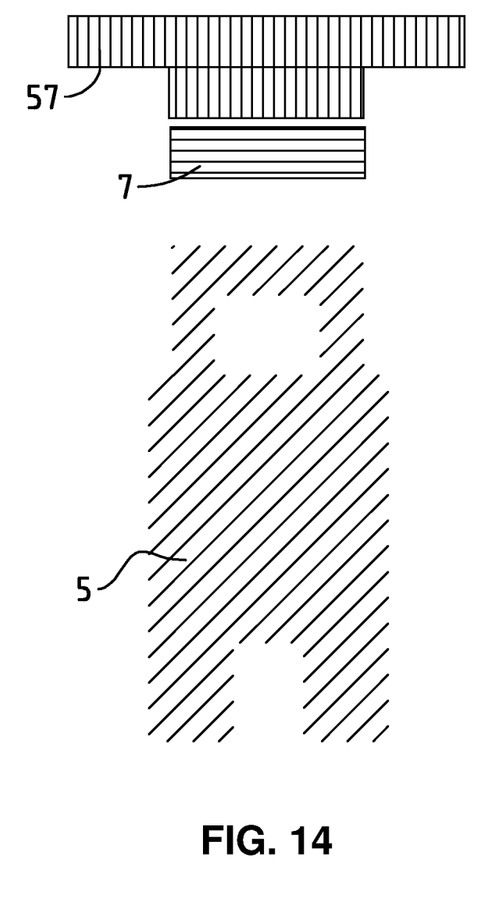
FIG. 14 shows a drawing according to a sectional view of a plunger and a magnet according to another preferred embodiment in which the push-button is provided with a magnetic shielding.

FIG. 14 shows, finally, for its part, a drawing according to a sectional view of a plunger 5 and a permanent magnet 7 according to a variant relating to the preferred embodiment in which the permanent magnet is integrated in the push-button 61—as illustrated in particular in FIGS. 5 to 7 and 8 to 10—in which the push-button 61 is provided moreover with a magnetic shielding. To this end, the permanent magnet 7 is covered by a shielding cover 57, made, for example, in Mu-metal, and which is integrated in said push-button, either by constituting the material of the push-button 61 itself, or an inner fitting.

Although the invention relating to a new clamping device improved by means of the exertion of a magnetic force acting upon the plunger to keep it in a high position, preventing any loosening of the clamp, has been described in connection with distinct embodiments illustrated by the preceding sets of figures, it will be understood that a combination in particular of two preferred embodiments relating to turbines is conceivable with a view to maximize the strength of the force of magnetic attraction F upward in direction of the push-button 61. Furthermore, it will be likewise understood that the anti-heating ball 8 could be implemented in ferromagnetic material for any of the embodiments described in the foregoing, including those relating to the contra-angle illustrated in FIGS. 8 to 10.

One skilled in the art will understand moreover that it is likewise conceivable to arrange the clamping device and the mutually co-operating magnetic pieces not in the head 10 of the handpiece 1 as a whole, but in a module or a cartridge intended to be installed in the head.

However, in view of the preceding explanations and the technical effect sought, it will be understood that it would be disadvantageous to arrange a permanent magnet 7 directly in the plunger 5 and to reverse the disposition of the ferromagnetic pieces in the plunger module 6, because since the clamp 4 is most of the time implemented also in a ferromagnetic material, the mutual magnetic attraction between the plunger 5 and the clamp would have the opposite effect of that sought.

For all the illustrated embodiments, a particularly advantageous variant consists furthermore in manufacturing the plunger in an iron alloy whose hardness is less than or equal to 800 HV and covered by a thin hard coating whose hardness is equal to or greater than 900 HV. By way of non-limiting example, the plunger can be made of martensitic stainless steel or of a cobalt-iron alloy. In this way, the resistance to corrosion, the magnetic permittivity and the magnetic saturation of the body of the plunger can be maximized through the use of relatively less hard material (typically 150-700 HV for martensitic tempered or non-tempered steels, or other non-corrosive highly ferromagnetic iron-cobalt alloys such as Vacoflux®). By way of non-limiting example, the hard layer can be achieved in chromium nitride or titanium nitride or tantalum nitride or silicon oxide and can be deposited by PVD or CVD or ALD technology. In this way, the wear-resistance of the plunger-clamp and plunger-shaft contact surfaces is maximized, and consequently the service life is increased.

For all the illustrated embodiments, a particularly advantageous variant consists moreover in manufacturing the plunger by machining, by cutout or 3D printing in a composite material made up of a component of low density, less than or equal to 5 g/cm$^3$ (by way of example, silicon or polypropylene or another resin), with the inclusion of powders of ferromagnetic material having a field of magnetic saturation equal to or greater than 1 T (by way of example, iron, cobalt or nickel). The advantage of this variant is that the plunger can be at the same time very light and be affected by a very strong force of magnetic attraction toward the magnet, while favoring the keeping of the plunger in elevated position with respect to the clamp, even in the case of very intense shocks. Possible implementations of this variant can be derived by one skilled in the art on the basis of the following articles:

Fiske, T. J., Gokturk, H. S. & Ka lyon, D. M. *Journal of Materials Science* (1997) 32: 5551. https://doi.org/10.1023/A:1018620407013, Materials Science and International Team (2008).

Selected Systems from C—Cr—Fe to Co—Fe—S. Springer, p. 22 (FIG. 2 Phase diagram of the Fe—Si system), DOI: 10.1007/978-3-540-74196-1_12. ISBN 978-3-540-74193-0, retrieved 25 Dec. 2011.

For all the illustrated embodiments, a particularly advantageous variant consists in introducing in the push-button an insert, visible from the outside, made up of a magnetostrictive or magnetochromatic material and/or fluid, that is to say whose form and/or color varies as a function of the outer magnetic field. By way of non-limiting example, examples of these families of materials can be found in the following documents:

Zhuang, Lin et al., "Hydrophilic Magnetochromatic Nanoparticles with Controllable Sizes and Super-high Magnetization for Visualization of Magnetic Field Intensity", *Scientific Reports*, 2015 Nov. 23/online, 5, 17063, https://doi.orq/10.1038/srep17063, https://www.nature.com/articles/srep17063#supplementary-information Diane Talbot, *Smart Materials*, booklet produced as the 2003 resource for the Institute of Materials, Minerals and Mining Schools Affiliate Scheme Advantageously the material and/or the fluid thus inserted in the push-button and visible from outside can indicate to the user or the technician, during a repair in the context of after-sales service, the degradation of the magnetic field produced by the magnet, this degradation due either to the degradation and/or aging of the magnet (being subjected to sterilization procedures not in keeping with the instructions for use of the product, too high a temperature or high vacuum), or to the penetration into the head of the turbine of strongly magnetic materials able to distort the field lines, or a violent shock having broken the magnet or the plunger. In this case, the user will be able to return the handpiece for repair before causing the degradation of other internal components, and/or the after-sales technician will be able to intervene specifically to clean and/or repair the magnetic components of the handpiece.

The invention claimed is:

1. Handpiece for dental or surgical applications, comprising:
a head in which is inserted in removable fashion a drilling tool adapted to be actuated in rotation about an axis of rotation by means of a drive mechanism comprising a drive shaft rotating about said axis of rotation,
a clamping device for said drilling tool, comprising a chucking clamp disposed inside said drive shaft for axial retention of said drilling tool with respect to said axis of rotation, said clamp co-operating with a plunger,
a push-button arranged to act upon said plunger in order to release said drilling tool, and
a permanent magnet arranged symmetrically around said axis of rotation and exerting a force of magnetic attraction on said plunger in a direction of said push-button.

2. Handpiece according to claim 1, said permanent magnet having an annular or cylindrical shape.

3. Handpiece according to claim 1, said push-button being held in said head by a retaining nut, said permanent magnet being arranged on said retaining nut.

4. Handpiece according to claim 3, said permanent magnet being fixed to said retaining nut of said push-button by means of a retaining piece provided with an axial retaining collar.

5. Handpiece according to claim 1, said permanent magnet being unified with the said push-button.

6. Handpiece according to claim 5, said permanent magnet being disposed between an axial retaining washer and a lower face of said push-button.

7. Handpiece according to claim 6, said axial retaining washer being made of a ferromagnetic material.

8. Handpiece according to claim 5, an anti-heating ball being arranged in the push-button, said anti-heating ball being made of a ferromagnetic material.

9. Handpiece according to claim 5, said permanent magnet being formed by a pad disposed in a recess of a lower face of said push-button, adapted to come into contact with an anti-heating ball arranged in an upper part of said plunger integral in rotation with said drive shaft.

10. Handpiece according to claim 5, further comprising a cover made of Mu-metal covering said permanent magnet.

11. Handpiece according to claim 1, said plunger further comprising a first peripheral annular protrusion extending upward.

12. Handpiece according to claim 1, said plunger further comprising a peripheral annular protrusion extending in radial direction beyond a shoulder.

13. Handpiece according to claim 1, said plunger being covered by a cap comprising magnetic material, said cap having an annular bead extending in both an axial direction and a radial direction.

14. Handpiece according to claim 1, the said plunger being made of an iron alloy the hardness of which is less than or equal to 800 HV and covered by a thin hard coating the hardness of which is equal to or greater than 900 HV.

15. Handpiece according to claim 1, the said plunger being manufactured by machining, cutout or 3D printing in a composite material made up of a component of low density, less than or equal to 5 $g/cm^3$, with inclusion of powders of ferromagnetic material having a field of magnetic saturation equal to or greater than 1 T.

* * * * *